United States Patent [19]
Abela et al.

[11] Patent Number: 5,620,439
[45] Date of Patent: Apr. 15, 1997

[54] CATHETER AND TECHNIQUE FOR ENDOVASCULAR MYOCARDIAL REVASCULARIZATION

[75] Inventors: George S. Abela, 80 Longfellow Rd., Wellesley, Mass. 02181; H. Paul Maruska, Acton, Mass.

[73] Assignees: George S. Abela, E. Lansing, Mich.; Spire Corporation, Bedford, Mass.

[21] Appl. No.: 468,474

[22] Filed: Jun. 6, 1995

[51] Int. Cl.$^6$ ................................................. A61B 17/36
[52] U.S. Cl. ................................ 606/11; 606/15; 606/17
[58] Field of Search ...................... 606/2, 10, 11, 606/12, 14, 15, 16, 17

[56] References Cited

U.S. PATENT DOCUMENTS

| | | |
|---|---|---|
| 4,852,567 | 8/1989 | Sinofsky . |
| 4,860,743 | 8/1989 | Abela . |
| 4,965,803 | 10/1990 | Esterowitz et al. . |
| 4,967,416 | 10/1990 | Esterowitz et al. . |
| 4,969,150 | 11/1990 | Esterowitz et al. . |
| 5,003,547 | 3/1991 | Esterowitz et al. . |
| 5,014,279 | 5/1991 | Esterowitz et al. . |
| 5,037,421 | 8/1991 | Boutacoff et al. . |
| 5,061,265 | 10/1991 | Abela et al. . |
| 5,084,880 | 1/1992 | Esterowitz et al. . |
| 5,086,432 | 2/1992 | Esterowitz et al. . |
| 5,107,509 | 4/1992 | Esterowitz et al. . |
| 5,200,966 | 4/1993 | Esterowitz et al. . |
| 5,206,867 | 4/1993 | Esterowitz et al. . |
| 5,268,920 | 12/1993 | Esterowitz et al. . |
| 5,380,316 | 1/1995 | Aita et al. . |
| 5,389,096 | 2/1995 | Aita et al. . |
| 5,468,238 | 11/1995 | Mersch .................................. 606/15 |

FOREIGN PATENT DOCUMENTS

| | | |
|---|---|---|
| 0515867 | 4/1992 | European Pat. Off. . |

OTHER PUBLICATIONS

"Transvascular Argon Laser–Induced Atrioventricular Conduction Ablation in Dogs" (Abstract), Circulation, Part II, vol. 68, No. 4, Oct. 1983, p. III–145.

"Transvascular Argon Laser Ablation of Atrioventricular Conduction in Dogs: Feasibility and Morphological Results"; Curtis, Abela, Griffin, Hill, and Normann; Laser Ablation of Atrioventricular Conduction, pp. 347–357, vol. 12, Feb. 1989.

"Modification of Atrioventricular Conduction Using a Combined Laser–Electrode Catheter;" Curtis, Mansour, Friedl, Tomaru, Barbeau, Normann, & Abela; Laser Ablation of AV Junction, pp. 337–348, vol. 17, Mar. 1994.

"Evaluation of Optical Properties and Laser Effects on Arterial Tissue Using a Microlens Tipped Optical Fiber", Barbieri et al, SPIE, vol. 713, Optical fibers in Medicine II, 1986, pp. 166–169.

"Myocardial Revascularization by Laser–Induced Channels", Jeevanandam et al, Surgical Forum XLI, Oct. 1990, pp. 225–226.

(List continued on next page.)

*Primary Examiner*—Angela D. Sykes
*Assistant Examiner*—Sonya Harris-Ogugua
*Attorney, Agent, or Firm*—William L. Feeney; Kerkam, Stowell, Kondracki & Clarke, P.C.

[57] ABSTRACT

A laser treatment device provides an output operating laser beam having a single wavelength which is highly absorbed by tissue of a patient and which beam is non-diverging. The laser treatment device may be a catheter which is inserted into a patient for performing endovascular myocardial revascularization (i.e., creating new channels for blood flow from within the interior of the patient's heart). The use of the highly absorbed wavelength and the non-diverging character of the beam are possible by having a distal laser at a distal end of the catheter. The distal laser is pumped by a source of laser energy supplied by an array of diode lasers and passed along an optical fiber from a proximal end of the catheter.

35 Claims, 3 Drawing Sheets

OTHER PUBLICATIONS

"Coherent Receives Patent On Arthroscopic Laser", Press Release, Ahmad Abu–Shumays, Aug. 15, 1991, No. 453, 2 page document.

Lasers in Cardiovascular Medicine and Surgery: Fundamentals and Techniques, Mirhoseini and Cayton, Edited by: George Abela, "Direct Myocardial Revascularization: Preliminary Experience," pp. 394–395.

CATHETER AND TECHNIQUE FOR ENDOVASCULAR MYOCARDIAL REVASCULARIZATION

BACKGROUND OF THE INVENTION

The present invention relates to a catheter and technique for application of laser energy to a patient. More specifically, it relates to a catheter and technique for endovascular myocardial revascularization. In other words, it involves use of a device within a patient's heart to create channels other than the coronary arteries, which channels can supply oxygenated blood and remove waste products from the myocardial tissue.

Myocardial infarctions (heart attacks) are the major pathological killer in America, resulting in the deaths of more than 500,000 persons each year. The flow of blood is compromised as atherosclerotic plaques develop within the coronary arteries, constricting their diameter, and quite often death ensues due to the complications inherent with the ischemia or infarction of the myocardium. Despite important advances which have been made in preventing and treating atherosclerotic cardiovascular disease, coronary artery impairments continue to constitute a major health problem. The most pervasive method of treating acute coronary artery occlusions is bypass surgery; however, opening of the thoracic cavity entails great pain and risks for the patient.

An alternative to bypass surgery is percutaneous transluminal angioplasty (using balloons, lasers, or a combination), a technique for delivering an object capable of removing lesions from affected arteries via a catheter. Serious possible side effects include acute closure or rupture of the blood vessel. Furthermore, there are significant numbers of afflicted individuals who are not candidates for either of these therapeutic procedures for the treatment of myocardial ischemia. These include patients with severe small-vessel diseases, diabetes, and those who could not withstand the trauma of cardiopulmonary bypass. More advanced techniques would be welcome for handling these cases, especially a means for the direct recanalization of the afflicted myocardium.

In the procedure known as balloon angioplasty, a thin catheter which contains at its distal end a tiny deflated balloon is threaded through an artery to the location of blockage. When in place in the region of occlusion, the balloon is inflated, and the obstructing plaque in the blood vessel is compressed against the arterial wall. This procedure is much less costly and traumatic to the patient than coronary bypass surgery. Many patients have been subjected to this therapy, and many of them have been relieved of symptoms. Unfortunately, it is often found that restenosis occurs over time because, basically, nothing has been removed from the artery. Although some patients receive a long term cure, others find that blockage reoccurs in about six months time.

There have been a number of reports of attempts to vaporize atherosclerotic plaque using laser radiation delivered to the site of the occlusion through flexible optical fibers carried within a catheter. While the long-wavelength Er and $CO_2$ lasers may be well suited to the task, fibers presently available do not concurrently meet transmission specifications, required cost levels, and flexibility requirements. Roughly 30% of laser procedures presently result in either perforation or dissection of the vessel, and restenosis due to wall damage remains a significant cause of failure during long-term follow up.

As an alternative procedure, direct myocardial revascularization can provide a supply of channels other than the coronary arteries to supply oxygenated blood and remove waste products from the myocardial tissue. Because the heart has the ability to use conduits and communicating channels to perfuse itself, several different approaches have been taken for exploring the possibility of direct revascularization of the ischemic myocardium. Techniques of revascularization are disclosed in U.S. Pat. No. 5,061,265 issued to Dr. George S. Abela and hereby incorporated by reference. One revascularization technique attempted to introduce collateral circulation using myopexy (roughening the myocardial surface to enhance capillarization) and omentopexy (sewing the omentum over the heart to provide a new blood supply). Another approach involved implanting the left internal mammary artery directly into heart muscle so that blood flowing through side branches of this artery could perfuse the muscle. The blood was distributed by sinusoids and communicating networks within the myocardium. Similar techniques have involved polyethylene tubes, endocardial incisions, the creation of channels with various types of needles, and needle acupuncture.

The needle acupuncture approach rests on the critical observation that in the hearts of vipers and reptiles, myocardial perfusion occurs via communicating channels between the left ventricle and the coronary arterial tree. Thus there exist central channels in the reptilian heart that radiate from the ventricular cavity and perfuse the thickness of the myocardial wall during systole. Reptiles do not have to rely on the functioning of coronary arteries in the same manner as mammals must. This finding is the central thesis underlying attempts to duplicate the reptilian vascular pattern in the mammalian heart. However, it has been shown that the channels formed by acupuncture all close within two or three months due to fibrosis and scaring. Therefore such mechanical techniques have been largely abandoned in favor of the use of lasers to effect transmyocardial canalization. The most important advantage of channels created by a laser is that there is no mechanical injury to the heart muscle, because the channels are created by vaporization. Reports indicate that in laser canalization, fibrosis and scaring are limited, and the laser-produced channels remain patent for more than two years.

The unique properties possessed by certain types of lasers that can be applied to myocardial revascularization include removal of tissue by vaporization; high absorption of the light wave by biological tissue; rapid vaporization with little thermal damage to surrounding tissue; and precise selection of the tissue to be removed. Studies based on using the $CO_2$ laser to create channels relied on penetration of the wall of the heart by focussing the laser on the epicardium and ablating tissue until the endocardium was penetrated. Studies on mongrel dogs indicated that a 400 W $CO_2$ laser was able to penetrate through the wall of the heart in microseconds, and that channel size could be controlled by the external optical system. When the canine hearts were later examined, it was found that epicardial sites of the laser channeling were marked by dots of fibrous tissue, which apparently is able to heal the outer surface punctures and prevent chronic bleeding. These plugs only penetrated about one millimeter into the channel, so the revascularization was successful. Early results on human subjects also appear to be promising. However, conventional surgical procedures were required, including opening of the chest cavity and cardiopulmonary bypass.

There are several problems associated with passing laser energy through an optical fiber to reach the heart or any inside part of a patient. If laser energy passes from the proximal end (i.e., input end, outside of patient) to the distal end of an optical fiber catheter within a patient, the laser energy looses some of its coherence. It will spread as a conical beam upon exiting the distal end or tip of the optical fiber. Since its power density distribution drops off with the square of the radius, any tissue offset sufficiently from the tip will be subject to a beam of lower power density. This may result in undesirable burning, charring, and/or heating of the tissue, instead of the ablation of the tissue desired under various circumstances. This may prevent or minimize the effectiveness of a given medical procedure, especially where the spreading or diffusion of the laser beam causes it to strike healthy tissue adjacent to the desired target. In cardiovascular applications, the burning, charring, and heating may inhibit desired growth of spongy tissue at the treated sites.

Another problem with applying lasers internally to a patient is that the wavelengths of light which will pass through a regular optical fiber catheter do not include the wavelength which the body tissues will most readily absorb. Using other wavelengths of light increases the risk that the laser beam energy will puncture the wall of a vessel or other body tissue before the laser energy is completely absorbed. In other words and for example, a laser beam which must pass through 2 millimeters of tissue before complete absorption is more likely to puncture than one which is completely absorbed in 1 millimeter. The relatively slow drop off of power in the beam direction of such less than ideal wavelengths for absorption makes it difficult to precisely control the depth of the ablation or the resulting hole. One can decrease the danger of puncture by reducing the beam power, but this may increase the problem of low power density causing undesirable burning, charring, and/or heating of the tissue, instead of the ablation of the tissue. (Notwithstanding some of these problems, the incorporated by reference '743 disclosed in both its background and its various designs the use of lasers for recanalization, among other uses.)

Recent developments of zirconium fluoride and sapphire fibers have been described as paving the way for possible endoscopic applications of short penetration depth lasers, but use of non-standard optical fibers introduces possible problems. Moreover, such suggestions would still require passage of the treatment beam (i.e., laser beam which actually strikes the patient's tissues) through fibers which cause loss of coherence and beam spreading.

The direct application (i.e., without passage through an optical fiber) of a laser beam to a patient's tissue such as the heart for revascularization avoids the spreading of the beam and associated problems, but requires major surgery such as, in the case of revascularization, opening of the chest cavity. This increases the risk to the patient. In the case of revascularization by transmyocardial canalization, the laser beam is directly applied to the outside of a heart and is used to create a channel extending into the interior of the heart (i.e., a through channel). This causes bleeding and later clotting may or may not significantly block the channel which was formed. Although some early results are promising, there is still a danger that the clotting will negate the benefits of the created channels.

OBJECTS AND SUMMARY OF THE INVENTION

Accordingly, it is a primary object of the present invention to provide a new and improved catheter and associated method for application of laser energy to a patient. (As used herein, a patient may be a human or animal patient.)

A more specific object of the present invention is to provide a catheter and technique for endovascular myocardial revascularization.

A further object of the present invention is to provide laser treatment of a patient with a wavelength allowing precise control of the depth of penetration by a laser beam and allowing precise control of the width of application of the beam (i.e., no or minimal spreading of the beam).

Yet another object of the present invention is to provide laser treatment of diseased tissue of a patient with minimal impact on adjacent tissues.

A further object of the present invention is to provide direct myocardial revascularization without the need for opening the chest cavity.

Yet another object of the present invention is to provide direct endovascular myocardial revascularization without having to create a through channel with its associated bleeding and potential for clots damaging its effectiveness.

The above and other features of the present invention which will be more readily understood when the following detailed description is considered in conjunction with the accompanying drawings are realized by a catheter for treating a patient. The catheter has a proximal end interface for receiving pump laser energy external to a patient. An optical fiber is connected to the proximal end interface and extends towards a distal end. A catheter body extends from the proximal end to the distal end. A distal operating laser is mounted at the distal end and operable to receive laser energy from the optical fiber and operable to use the received laser energy as pumping energy to generate an output laser beam exiting directly from the catheter. The output laser beam has a wavelength different from the pumping energy.

The output laser beam is a beam with a wavelength of from 2.5 to 3.1 microns. More preferably, the output laser beam is a single mode beam with a wavelength of from 2.7 to 2.9 microns. Even more preferably, the output laser beam is a single mode beam with a wavelength of 2.808 microns. The distal laser has Er as an emitter. The distal laser can be constructed of any material which can host erbium ions such that the erbium ions are allowed to emit coherent radiation with a single wavelength in the range of 2.7 to 2.9 microns.

The output laser beam is suitable for endovascular myocardial revascularization, meaning that a surgeon would find that its width and divergence allowed its use for endovascular myocardial revascularization. The output laser beam exits from a side of the catheter body and the output laser beam extends no more than 180 degrees (more preferably no more than 90 degrees, even more preferably no more than 45 degrees) in the circumferential direction about the device body adjacent the distal end. The divergence of the output laser beam is no more than 20 mrads, more preferably no more than 10 mrads. The width of the output laser beam as it leaves the catheter is no more than 1.5 mm, preferably no more than 1.0 mm.

An outer hood is mounted to the catheter body adjacent the distal end and having an opening disposed therein, the opening disposed to allow the output laser beam to pass therethrough. A flushing solution channel is interior to the catheter body and connected to supply flushing solution to the opening. An inner hood is within the outer hood and at least an exit part of the distal laser being disposed within an interior of the inner hood, the interior being sealed to prevent flushing solution from entering therein.

The proximal end interface is an optical integrator. The optical integrator is operably connected to receive laser energy from at least one diode laser bar.

In a first embodiment, the distal laser is oriented to supply the output laser beam in a lengthwise (axial) direction relative to the catheter. In a second embodiment, the distal laser is oriented to supply the output laser beam in a sideways (transverse) direction relative to the catheter.

The present invention may alternately be described as a laser treatment device for applying laser energy to a patient. The device has a proximal end interface for receiving pump laser energy external to a patient. An optical fiber is connected to the proximal end interface and extends towards a distal end. A device body extends from the proximal end to the distal end. A distal operating laser is mounted at the distal end and operable to receive pump laser energy from the optical fiber and operable to use the received laser energy as pumping energy to generate an output laser beam exiting from the device.

The present invention may alternately be described as a method including the steps of:

placing the laser treatment device described above in a treatment position relative to a patient;

applying laser energy to the proximal end interface such that the applied laser energy will pass along the optical fiber to serve as pumping energy to the distal laser; and applying an output laser beam from the device to the patient.

In the preferred technique, the device is a catheter and the device body is a catheter body, and the placing step is accomplished by inserting the catheter in the patient. More specifically, the output laser beam is applied to the patient to effect revascularization interior to a heart of the patient.

The present invention may alternately be described as a method including the steps of:

placing the above described catheter in a treatment position within a patient; and applying an output laser beam from the device to the patient, and wherein the output laser beam has a wavelength of from 2.5 to 3.1 microns.

The output laser beam is applied to the patient to effect revascularization interior to a heart of the patient.

BRIEF DESCRIPTION OF THE DRAWINGS

The above and other features of the present invention will be more readily understood when the following detailed description is considered in conjunction with the accompanying drawings wherein like characters represent like parts throughout the several views and in which.

DETAILED DESCRIPTION

Figure 1:
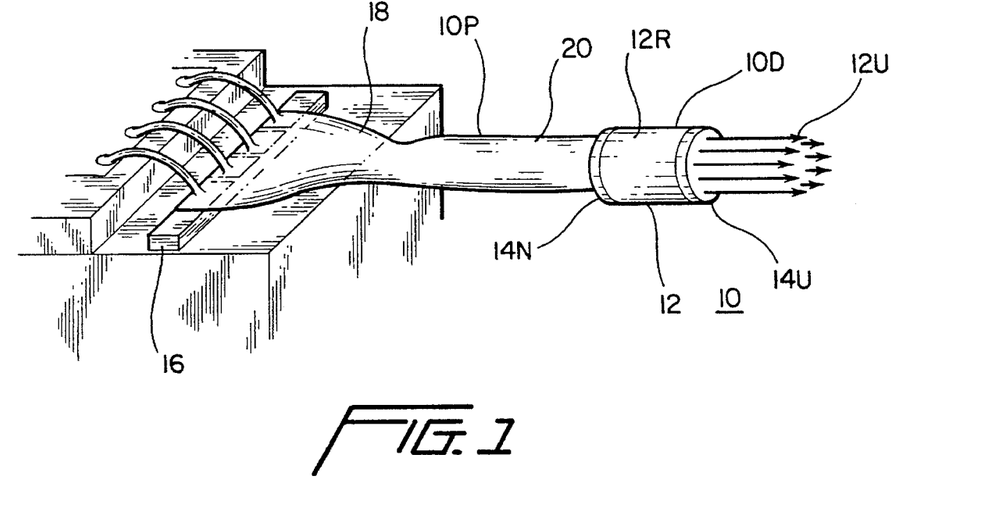
FIG. 1 is simplified perspective illustrating the principles of operation of the laser treatment device of the present invention.

FIG. 1 shows a simplified perspective illustrating some features of the laser treatment device or catheter 10 according to the present invention. The catheter 10 has a distal end 10D and a proximal end 10P. A solid state distal end laser 12 has a rod 12R of Er:YLF (erbium is the emitter, yttrium lithium fluoride is the host) material disposed between an input mirror 14N and an output mirror 14U.

The input mirror 10N receives pumping energy from at least one diode laser bar 16 by way of a proximal end interface such as ribbon fiber optical integrator 18 and a 400 micron diameter core quartz optical fiber 20. Preferably, more than one diode laser bar would be used, but only one is shown for ease of illustration. Although not shown, there preferably would be a focussing lens between bar 16 and integrator 18, the lens preferably having a diameter of at least 1 cm and a focal length of 1 cm or less.

Pumping of the Er:YLF solid state laser 12 can be accomplished with the lasers of laser bar 16 emitting at 797 nanometers (0.797 microns). Absorbed photons at that wavelength leads to electron excitement in the erbium such that the laser is ready for emission of photons at 2.8 microns.

The use of diode lasers as pump sources for solid state lasers provide a higher efficiency of power transfer, generally leading to simple, compact structures, as has been appreciated for some time. Recent improvements in growth and fabrication techniques for diode lasers increase the desirability and feasibility of use of diode lasers as pump sources.

Diode pumped solid state lasers provide three advantages over the direct use of diode lasers. First, solid state lasers generally possess much larger transverse and lateral dimensions than diode lasers. This allows beam divergence (expansion) to be much smaller (mrads) without needing to resort to external optics for beam collimation. (In other words, the beam starts out sufficiently wide and collimated for treatment purposes.) Second, a solid state laser inherently tends to operate at a single wavelength with a very narrow spectral linewidth. Third, a solid state laser usually has a long excited state lifetime, allowing the collection of energy from an array of diode lasers over time, with subsequent release as a very high peak power pulse. Much previous work has focused on pumping the Nd:YAG laser, emitting at either 1.06 or 1.32 microns.

The laser bar 16 would preferably be high power AlGaAs lasers emitting at 797 nanometers, which corresponds to the proper wavelength for direct pumping of the upper laser state of the erbium ion. This pumping energy wavelength is at a high absorption coefficient on the absorption spectrum for $Er^{3+}$, although other points on the spectrum might be used for the pumping energy.

The pumping energy at 797 nanometers enters laser 12 by way of dielectric mirror 14N, which is transmitting at 797 nanometers (0.797 microns) and 100% reflecting at 2.8 microns. The rod 12R of Er:YLF is preferably about 1 millimeter in diameter and 8 millimeters in length. The output dielectric mirror 14U, which also serves as a round collimating lens, is 100% reflecting at 797 nanometers and is about 99 to 99.5% reflecting at 2.8 microns.

Advantageously, the pumping energy is at a wavelength which can pass along a regular optical fiber such as a quartz fiber. At the same time, the catheter provides the 2.8 micron (more accurately 2.808 micron) wavelength energy which is most useful for providing good depth resolution in the application of energy to tissues of a patient. Furthermore, the fact that the lasing action occurs within the distal laser 12 at the distal end 10D of the catheter 10 means that the coherence is not degraded by passage of the 2.8 micron energy along an optical fiber and means that the single mode 2.8 micron output beam 12U has ultra-low divergence (i.e., much less beam spreading than would otherwise occur). The low divergence means that the energy density does not diminish in the fashion which might cause burning, charring, and/or heating at the edge of the energy application as discussed above.

Therefore, the operating laser 12 shifts the wavelength of the pump energy applied to it, provides great coherence in its output, and provides an ultra-low divergence beam of an appropriate width.

Preferably, the pump laser energy is pulsed to take advantage of the depth resolution by allowing one to carefully control the depth of revascularization, removal of HIS tissues, ablation of clotted arteries, or other application of laser energy to patient tissue. For example, if one wanted to remove 10 microns of tissue and the energy density and pulse length were such that each pulse removes 2 microns, 5 pulses would be applied to get the required material removed.

Figure 2:
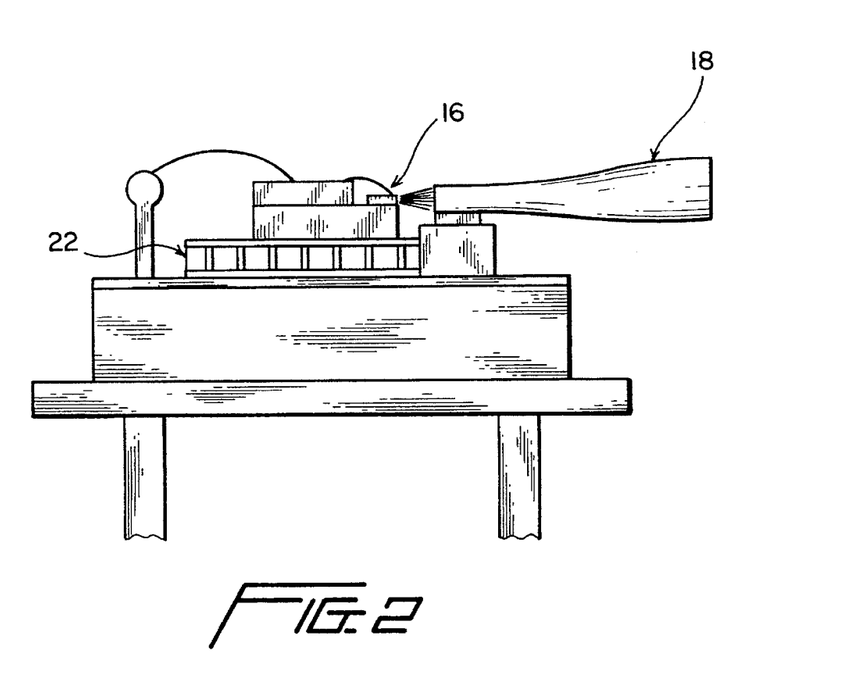
FIG. 2 is a simplified side view showing proximal end components.

With reference to FIG. 2, the basic concept for collecting the output of the laser bar 16 into a fiber involves the use of fiber ribbons to alter the high aspect ratio emission from the bar, filling the aperture of a square waveguide. This functionality can be accomplished by placing fiber ribbons, each 25 microns high by 250 microns wide, in position sequentially across the near-field emission pattern of the bar 16. Each ribbon will then be twisted by 90 degrees, and they will all be fastened together to form a square aperture 250 microns by 250 microns, which is effectively an optical integrator 18. The output of this optical integrator 18 is butt-coupled into a single circular fiber 20 (FIG. 1) with a 400 micron core. As mentioned previously, only one diode laser bar 16 is shown, but numerous bars could be used in a stack. A thermoelectric element 22 is used in the system, but more details of it, the bar 16, and integrator 18 (serving as a proximal end interface) need not be given since these structures are known to one of skill in this field.

Figure 3:
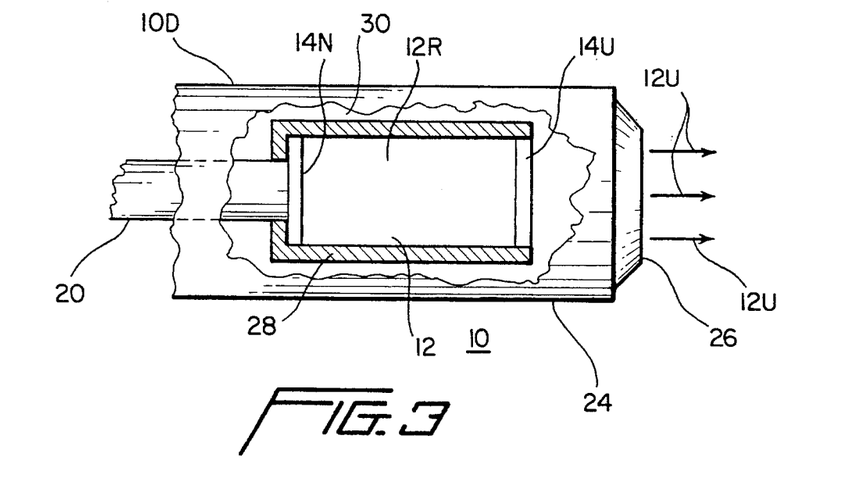
FIG. 3 is a side view of the distal end components of a first embodiment device or catheter of the present invention with a side of an outer hood broken away and an inner hood in cross section.

FIG. 3 shows how the laser 12 is mounted within an outer hood 24 having an output hole 26 through which the output beam 12U passes. Specifically, the laser 12 is inside of an inner hood 28 which in turn is inside of the outer hood 24 (which may be made of surgical stainless steel) and separated therefrom by a cylindrical flushing solution channel 30 which supplies flushing solution to the hole 26 such that blood or other body fluids do not burn against the mirror 14U. The mounting and use of the inner and outer hoods is described in U.S. Pat. No. 5,061,265, invented by one of the inventors herein, George S. Abela, M.D., together with Stephan E. Friedl. That patent is hereby incorporated by reference. If desired, the inner hood 28 may be a glass tube which is constructed and mounted as with the Abela '265 patent. Although not shown, it may extend around to cover the front of mirror 14U. Alternately, the inner hood 28 may be mounted as shown in Abela '265, but may have the front half of it (nearest mirror 14U) made of a gold plated copper shield and the back half of it made of regular catheter material. In that case, one could also have a cylindrical glass inner hood (not separately shown) around the half cooper shield/half catheter material cylinder.

In addition to preventing burned material from blocking the exit or output mirror 14U, the use of flushing solution supplied through channel 30 will help to prevent overheating of the laser 12.

Figures 4, 5:
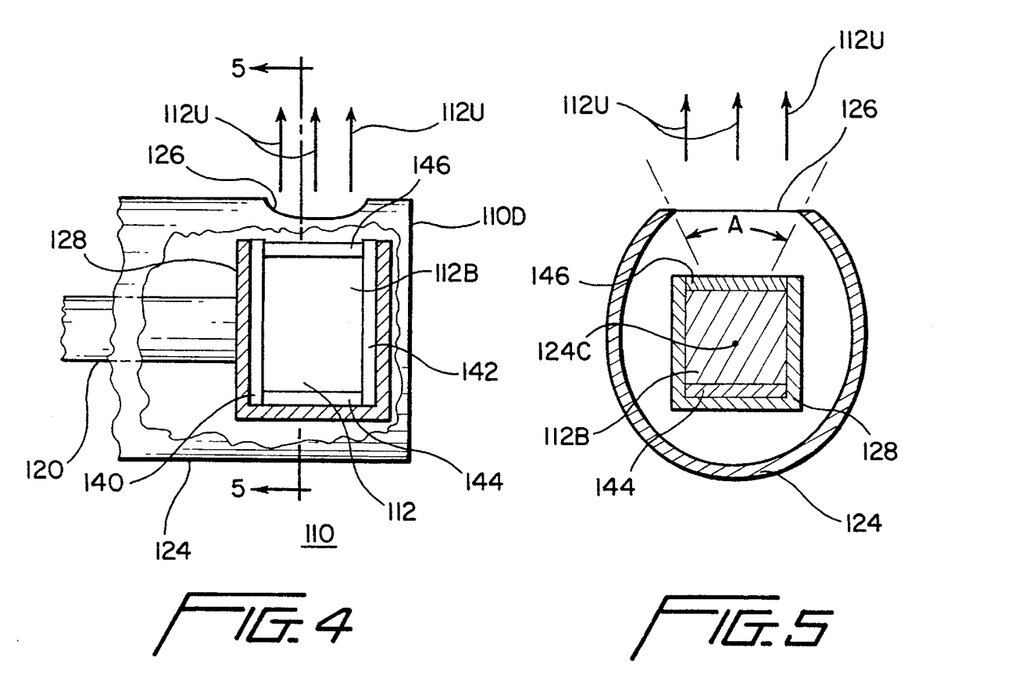
FIG. 4 is a side view of the distal end components of a second embodiment device or catheter with a side of an outer hood broken away and an inner hood in cross section.
FIG. 5 is a simplified cross section view taken along lines 5—5 of FIG. 4.

Turning now to FIGS. 4 and 5, the distal end of an alternate catheter 110 has components numbered in the 100 series with the same last two digits as the corresponding component, if any, from the first embodiment. Thus, the distal end 110D has an optical fiber 120 supplying pumping energy to a distal laser 112 within an outer hood 124. Outer hood 124 differs from hood 24 in that outer hood 124 has a side opening 126 from which output beam 112U has a direction transverse (more specifically perpendicular) to the lengthwise direction of the catheter 110. Beam 112U extends in a sideways direction.

In order to provide the output beam 112U with the proper orientation, input dielectric mirror 140 allows entry of the 797 nanometer pumping energy and opposite mirror 142 reflects the pumping energy. Between the mirrors 140 and 142, a parallelepiped or block of Er:YLF material produces lasing with back mirror 144 being 100% reflective at the 2.8 micron wavelength of the output energy and an output mirror 146 being about 99 to 99.5% reflective at 2.8 microns. An inner hood 128 may be constructed as discussed for hood 28 except that it may have a block shape.

The output laser beam 112U is suitable for endovascular myocardial revascularization, meaning that a surgeon would find that its width and divergence allowed its use for endovascular myocardial revascularization. As shown in FIG. 5, the output laser beam exits from a side of the catheter body and the output laser beam extends in an angle A in the circumferential direction about center 124C of catheter 124. The angle A is no more than 180 degrees (more preferably no more than 90 degrees, even more preferably no more than 45 degrees) in the circumferential direction about the device body adjacent the distal end. The divergence of the output laser beam is no more than 20 mrads, more preferably no more than 10 mrads. The width of the output laser beam as it leaves the catheter is no more than 1.5 mm, preferably no more than 1.0 mm. Note that angle A is not the divergence of the beam 112U, but instead is the angle of the beam width at the outer periphery of the catheter 124 relative to the central lengthwise axis 124C of the catheter. The suitability for endovascular myocardial revascularization, width and divergence of the lengthwise beam 12U of FIG. 3 is the same as discussed for the beam 112U of FIGS. 4 and 5 except that beam 12U is oriented in the lengthwise direction of the catheter, rather than the transverse or sideways direction.

Figure 6:
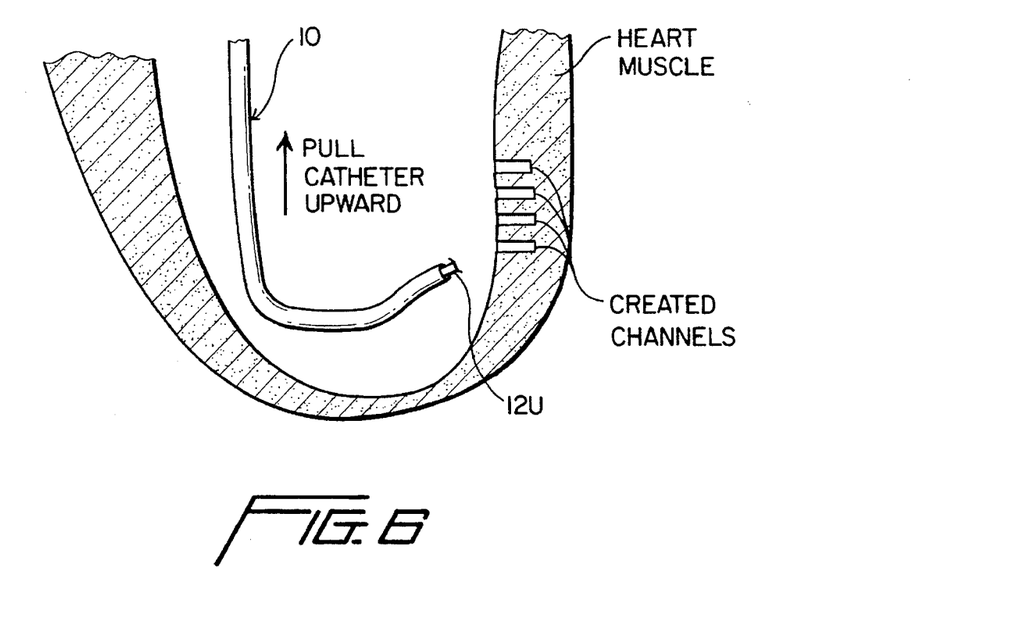
FIG. 6 is a simplified side view of the first embodiment in use.

With reference now to FIG. 6, the tip or lengthwise emitting catheter 10 provides the output beam 12U which may create the illustrated channels for revascularization of a patient's heart without open heart surgery being required. The catheter 10 may use spring biasing and an extendible catheter system (not shown) where a guide is anchored (hence the spring may be considered as an anchor) at the tip of the left ventricle and the extendible portion drills holes in the heart muscle from the inside outwardly in a radial as well as in sweeping arch manner. These features need not be described in detail since they are shown and discussed in U.S. patent application Ser. No. 08/123,207 filed Sep. 20, 1993 in the names of George S. Abela, Stephan E. Friedl, and Eric D. Mathews, which application is hereby incorporated by reference.

Figure 7:
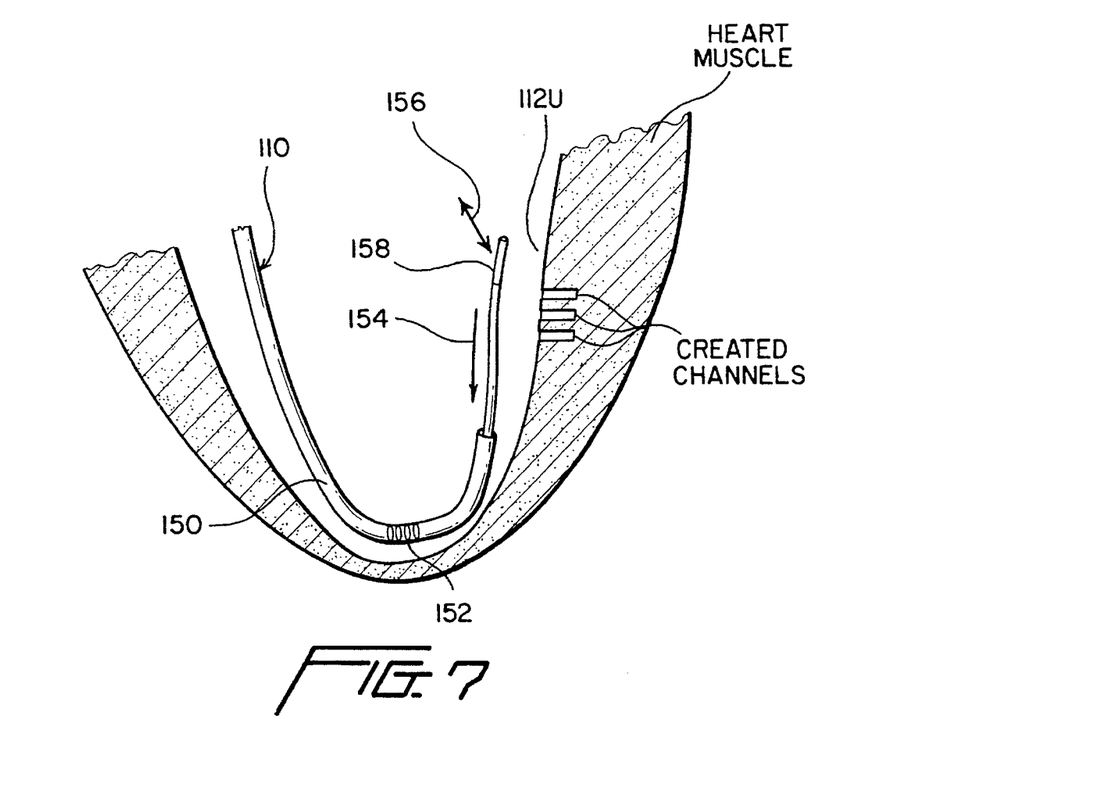
FIG. 7 is a simplified side view of the second embodiment in use.

FIG. 7 shows the side or transverse beam catheter 110 within a guiding catheter 150 biased by spring 152 (serving as an anchor to secure part of the outer or guiding catheter 150 to part of the interior surface of the heart) in the manner described in more detail in the incorporated by reference '207 application. Again, laser created channels are in the heart muscle. The sweeping feature for positioning is shown by arrow 156, whereas the extendibility for positioning is illustrated by arrow 154. This extendibility feature refers to lengthwise movement (along 154) of an inner catheter 158 relative to the outer catheter 150 such that the output laser beam can be applied to different parts or points in the heart while the anchoring part of the outer catheter is maintained at the same part or point in the heart. Although components 150 and 158 are referred to respectively as outer and inner catheters, they may alternately be considered as different outer and inner parts of a single catheter. Thus, laser energy may be applied at first, second, third, etc., points in the heart without reanchoring the outer catheter 150 by extending the inner catheter relative to the outer catheter 150 between repeated applications of laser energy. As discussed above, repeated pulses of laser energy may be applied to a given point in the heart for improved depth resolution such that the inner catheter would not necessarily be moved in between the time for each pulse, but would be moved only when the desired depth of material removal has occurred.

Although specific constructions have been presented herein, it is to be understood that these are for illustrative purposes only. Various modifications and adaptations will be apparent to those of skill in the art. In view of possible modifications, it will be appreciated that the scope of the present invention should be determined by reference to the claims appended hereto.

What is claimed is:

1. A catheter for treating a patient comprising:
   an optical fiber connected to the proximal end interface and extending towards a distal end; a catheter body extending in a lengthwise direction from a proximal end to a distal end and defining a circumferential direction around the lengthwise direction; an interface located at the proximal end for receiving laser energy external to a patient;
   a distal laser mounted at the distal end of the catheter body and operable to receive laser energy from the optical fiber and operable to use the received laser energy as pumping energy to generate an output laser beam exiting from the catheter;
   an outer hood mounted to the catheter body adjacent the distal end and having an opening disposed therein, the opening disposed to allow the output laser beam to pass therethrough; and
   a flushing solution channel interior to the catheter body and connected to supply flushing solution to the opening.

2. The catheter of claim 1 wherein the output laser beam has a wavelength different from the pumping energy.

3. The catheter of claim 2 wherein the output laser beam includes a wavelength of from 2.5 to 3.1 microns.

4. The catheter of claim 3 wherein the output laser beam is a single mode beam with a wavelength of from 2.7 to 2.9 microns.

5. The catheter of claim 4 wherein the output laser beam is a single mode beam with a single wavelength of 2.808 microns.

6. The catheter of claim 2 wherein the distal laser has Er as an emitter.

7. The catheter of claim 2 further comprising:
   an inner hood within the outer hood, at least an exit part of the distal laser being disposed within an interior of the inner hood, the interior being sealed to prevent flushing solution from entering therein.

8. The catheter of claim 7 wherein the distal laser has Er as an emitter.

9. The catheter of claim 7 wherein the proximal end interface is an optical integrator and further comprising at least one diode laser bar and the optical integrator is operably connected to receive laser energy from the at least one diode laser bar.

10. The catheter of claim 2 wherein the distal laser is oriented to supply the output laser beam in the lengthwise direction relative to the catheter.

11. The catheter of claim 2 wherein the distal laser is oriented to supply the output laser beam in a sideways direction relative to the catheter, the sideways direction being perpendicular to the lengthwise direction.

12. The catheter of claim 1 further comprising:
   an inner hood within the outer hood, at least an exit part of the distal laser being disposed within an interior of the inner hood, the interior being sealed to prevent flushing solution from entering therein.

13. The catheter of claim 1 wherein the output laser beam exits from a side of the catheter body, said output laser beam extending no more than 180 degrees in the circumferential direction about the device body adjacent the distal end and wherein the output laser beam is suitable for endovascular myocardial revascularization.

14. The catheter of claim 1 wherein the output laser beam is suitable for endovascular myocardial revascularization and wherein the output laser beam has a divergence of no more than 10 mrads.

15. A laser treatment device for applying laser energy to a patient comprising:
   an optical fiber connected to the proximal end interface and extending towards a distal end;
   a device body extending in a lengthwise direction from a proximal end to a distal end of the device body and defining a circumferential direction around the lengthwise direction; an interface located at the proximal end for receiving laser energy external to a patient, and
   a distal laser mounted at the distal end and operable to receive laser energy from the optical fiber and operable to use the received laser energy as pumping energy to generate an output laser beam exiting from a side of the device, said output laser beam extending no more than 180 degrees in the circumferential direction about the device body adjacent the distal end an outer hood mounted to the catheter body adjacent the distal end and having an opening disposed therein, the opening disposed to allow the output laser beam to pass therethrough.

16. The catheter of claim 15 wherein the output laser beam is suitable for endovascular myocardial revascularization.

17. The catheter of claim 16 wherein the output laser beam extends no more than 90 degrees in the circumferential direction about the device body adjacent the distal end.

18. The catheter of claim 17 wherein the output laser beam has a divergence of no more than 10 mrads.

19. The laser treatment device of claim 16 wherein the proximal end interface is an optical integrator and further comprising at least one diode laser bar and the optical integrator is operably connected to receive laser energy from the at least one diode laser bar and wherein the device is a catheter and the device body is a catheter body.

20. The laser treatment device of claim 15 further comprising:
   an outer hood mounted to the catheter body adjacent the distal end and having an opening disposed therein, the opening disposed to allow the output laser beam to pass therethrough;

a flushing solution channel interior to the catheter body and connected to supply flushing solution to the opening; and an inner hood within the outer hood, at least an exit part of the distal laser being disposed within an interior of the inner hood, the interior being sealed to prevent flushing solution from entering therein.

21. The laser treatment device of claim 15 wherein the output laser beam is a single mode beam with a wavelength of from 2.5 to 3.1 microns.

22. The laser treatment device of claim 21 wherein the output laser beam is a single mode beam with a wavelength of from 2.7 to 2.9 microns.

23. The laser treatment device of claim 22 wherein the output laser beam is a single mode beam with a wavelength of 2.808 microns.

24. A method comprising the steps of:

providing and inserting a laser treatment catheter in a treatment position in a patient, the laser treatment catheter having:

an optical fiber connected to the proximal end interface and extending towards the distal end of the catheter body;

a catheter body extending in a lengthwise direction from a proximal end to a distal end and defining a circumferential direction around the lengthwise direction; and a distal laser mounted at the distal end and operable to receive laser energy from the optical fiber and operable to use the received laser energy as pumping energy to generate an output laser beam exiting from the catheter an outer hood mounted to the catheter body adjacent the distal end and having an opening disposed therein, the opening disposed to allow the output laser beam to pass therethrough; applying laser energy to the proximal end interface such that the applied laser energy will pass along the optical fiber to serve as pumping energy to the distal laser; and applying an output laser beam from the catheter to the patient to effect revascularization interior to a heart of the patient, the output laser beam being suitable for endovascular myocardial revascularization.

25. The method of claim 24 wherein the output laser beam extends no more than 90 degrees in the circumferential direction about the catheter body adjacent the distal end.

26. The catheter of claim 24 wherein the output laser beam has a divergence of no more than 10 mrads.

27. The method of claim 24 wherein the output laser beam is a beam with a wavelength of from 2.5 to 3.1 microns.

28. The method of claim 27 wherein the output laser beam is a single mode beam with a wavelength of from 2.7 to 2.9 microns.

29. The method of claim 27 wherein the output laser beam is a single mode beam with a single wavelength of 2,808 microns.

30. A method comprising the steps of:

providing and inserting a laser treatment catheter in a treatment position inside the heart of a patient, the laser treatment catheter having:

an optical fiber connected to the proximal end interface and extending towards the distal end of the catheter body;

a catheter body extending in a lengthwise direction from a proximal end to a distal end and defining a circumferential direction around the lengthwise direction; and a distal laser mounted at the distal end and operable to receive laser energy from the optical fiber and operable to use the received laser energy as pumping energy to generate an output laser beam exiting from the catheter an outer hood mounted to the catheter body adjacent the distal end and having an opening disposed therein, the opening disposed to allow the output laser beam to pass therethrough;

applying laser energy to the proximal end interface such that the applied laser energy will pass along the optical fiber to serve as pumping energy to the distal laser; and applying an output laser beam from the catheter to an interior surface of the heart of the patient and wherein the output laser beam has a wavelength of from 2.5 to 3.1 microns.

31. The method of claim 30 wherein the output laser beam has a wavelength of from 2.7 to 2.9 microns.

32. The method of claim 31 wherein the output laser beam has a wavelength of 2.808 microns.

33. The method of claim 30 wherein the output laser beam is applied to the patient to effect revascularization interior to a heart of the patient.

34. The method of claim 33 wherein the catheter used in the method further includes:

a flushing solution channel interior to the catheter body and connected to supply flushing solution to the opening.

35. The method of claim 33 wherein the catheter used in the method further includes:

an outer catheter having an anchor thereon for securing the outer catheter to the heart, and an inner catheter movable in the lengthwise direction relative to the outer catheter; and wherein the method further comprises the steps of:

securing a part of the outer catheter to a part of the heart; repeatedly applying laser energy to the proximal end interface such that the applied laser energy will pass along the optical fiber to serve as pumping energy to the distal laser; repeatedly applying an output laser beam from the catheter to an interior surface of the heart of the patient; and after the application of the output laser beam to a first given location on the interior surface, moving the inner catheter relative to the outer catheter with the part of the outer catheter remaining at the part of the heart such that the output laser beam will strike a second given location on the interior surface.

* * * * *

UNITED STATES PATENT AND TRADEMARK OFFICE
CERTIFICATE OF CORRECTION

PATENT NO. : 5,620,439
DATED : April 15, 1997
INVENTOR(S) : George S. ABELA; H. Paul MARUSKA It is certified that error appears in the above-indentified patent and that said Letters Patent is hereby corrected as shown below:

Claim 29, line 2, (column 11, line 60), change "2,808" to -- 2.808 --.

Signed and Sealed this

Twelfth Day of August, 1997

Attest:

BRUCE LEHMAN

Attesting Officer   Commissioner of Patents and Trademarks